(12) United States Patent
Thompson

(10) Patent No.: US 6,205,840 B1
(45) Date of Patent: Mar. 27, 2001

(54) TIME CLOCK BREATHALYZER COMBINATION

(76) Inventor: Terry L. Thompson, 2880 Manor Rd., Coatesville, PA (US) 19320

( * ) Notice: Subject to any disclaimer, the term of this patent is extended or adjusted under 35 U.S.C. 154(b) by 0 days.

(21) Appl. No.: 09/238,602

(22) Filed: Jan. 28, 1999

(51) Int. Cl.[7] .............................. G01N 33/98; A61B 5/097
(52) U.S. Cl. .............................. 73/23.3; 422/84; 436/132; 436/900
(58) Field of Search ................... 73/23.3; 422/84; 438/132, 900

(56) References Cited

U.S. PATENT DOCUMENTS

| | | | |
|---|---|---|---|
| 3,792,272 | * | 2/1974 | Harte et al. .......................... 250/343 |
| 4,749,553 | * | 6/1988 | Lopez et al. ....................... 73/23.3 X |
| 4,809,810 | * | 3/1989 | Elfman et al. ................... 73/31.04 X |
| 5,458,853 | * | 10/1995 | Porter et al. ....................... 73/23.3 X |

* cited by examiner

Primary Examiner—Daniel S. Larkin

(57) ABSTRACT

A combined time clock breathalyzer is provided including a clock for tracking a current time, an inlet port, an alcohol sensor connected to the inlet port for determining an amount of alcohol in an air flow, and a printer. Also included is a controller adapted to calculate an alcohol percentage amount within a user from the amount of alcohol detected by the alcohol sensor. The controller is further adapted to provide an indication upon the alcohol percentage amount being greater than a predetermined amount.

7 Claims, 2 Drawing Sheets

TIME CLOCK BREATHALYZER COMBINATION

BACKGROUND OF THE INVENTION

1. Field of the Invention

The present invention relates to breathalyzers and more particularly pertains to a new time clock breathalyzer combination for preventing employees from working when having a blood alcohol level greater than an acceptable amount.

2. Description of the Prior Art

The use of breathalyzers is known in the prior art. More specifically, breathalyzers heretofore devised and utilized are known to consist basically of familiar, expected, and obvious structural configurations, notwithstanding the myriad of designs encompassed by the crowded prior art which have been developed for the fulfillment of countless objectives and requirements.

Known prior art includes U.S. Pat. No. 4,996,161; U.S. Pat. No. 4,818,489; U.S. Pat. No. 4,770,026; U.S. Pat. No. 2,591,691; U.S. Pat. No. 5,181,521; and U.S. Pat. Des. 368,037 which are each incorporated herein by reference.

In these respects, the time clock breathalyzer combination according to the present invention substantially departs from the conventional concepts and designs of the prior art, and in so doing provides an apparatus primarily developed for the purpose of preventing employees from working when having a blood alcohol level greater than an acceptable amount.

SUMMARY OF THE INVENTION

In view of the foregoing disadvantages inherent in the known types of breathalyzers now present in the prior art, the present invention provides a new time clock breathalyzer combination construction wherein the same can be utilized for preventing employees from working when having a blood alcohol level greater than an acceptable amount.

The general purpose of the present invention, which will be described subsequently in greater detail, is to provide a new time clock breathalyzer combination apparatus and method which has many of the advantages of the breathalyzers mentioned heretofore and many novel features that result in a new time clock breathalyzer combination which is not anticipated, rendered obvious, suggested, or even implied by any of the prior art breathalyzers, either alone or in any combination thereof.

To attain this, the present invention generally comprises a housing with a rectangular configuration having a front face, a rear face, a top face, a bottom face, and a pair of side faces. As shown in FIG. 1, the front face of the housing has a clock mounted thereon for tracking a current time and visually indicating the same. Further, a first one of the side faces has a plurality of vertically spaced horizontally oriented slots formed therein for storing a plurality of timecards therein. The front face has a flexible bellowed inlet tube with an inboard end coupled to the front face adjacent to the top face and a second one of the side faces. The top face further has a slot formed therein for releasably receiving one of the timecards. Situated within the housing is an air flow rate sensor that is connected to the inboard end of the inlet tube for determining a rate of air flow therethrough. Associated therewith is an alcohol sensor situated within the housing and connected to the inboard end of the inlet tube. In use, the alcohol sensor is adapted for determining an amount of alcohol in the air flow. Also positioned within the housing is a printer for printing characters on the timecard when inserted therein. As shown in FIG. 3, a controller is situated within the housing and connected to the air flow rate sensor, alcohol sensor, and printer. In use, the controller serves to calculate an alcohol percentage amount within a user from the amount of alcohol detected by the alcohol sensor. Such calculation is preferably carried out upon the detection of a sufficient air flow rate by the air flow rate sensor. The controller is further adapted to print the alcohol percentage amount and a time of beginning work upon a first insertion of one of the timecards within the slot of the housing. Upon a subsequent second insertion of the timecard within the slot of the housing, the controller is further adapted to print the alcohol percentage amount and a time of ending work. Note FIG. 4. Finally, alert indicia is printed on a cop of the timecard upon the alcohol percentage amount being greater than a predetermined amount.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions in so far as they do not depart from the spirit and scope of the present invention.

Further, the purpose of the foregoing abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new time clock breathalyzer combination apparatus and method which has many of the advantages of the breathalyzers mentioned heretofore and many novel features that result in a new time clock breathalyzer combination which is not anticipated, rendered obvious, suggested, or even implied by any of the prior art breathalyzers, either alone or in any combination thereof.

It is another object of the present invention to provide a new time clock breathalyzer combination which may be easily and efficiently manufactured and marketed.

It is a further object of the present invention to provide a new time clock breathalyzer combination which is of a durable and reliable construction.

An even further object of the present invention is to provide a new time clock breathalyzer combination which is susceptible of a low cost of manufacture with regard to both materials and labor, and which accordingly is then susceptible of low prices of sale to the consuming public, thereby making such time clock breathalyzer combination economically available to the buying public.

Still yet another object of the present invention is to provide a new time clock breathalyzer combination which provides in the apparatuses and methods of the prior art some of the advantages thereof, while simultaneously overcoming some of the disadvantages normally associated therewith.

Still another object of the present invention is to provide a new time clock breathalyzer combination for preventing employees from working when having a blood alcohol level greater than an acceptable amount.

Even still another object of the present invention is to provide a new time clock breathalyzer combination that includes a clock for tracking a current time, an inlet port, an alcohol sensor connected to the inlet port for determining an amount of alcohol in an air flow, and a printer. Also included is a controller adapted to calculate an alcohol percentage amount within a user from the amount of alcohol detected by the alcohol sensor. The controller is further adapted to provide an indication upon the alcohol percentage amount being greater than a predetermined amount.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
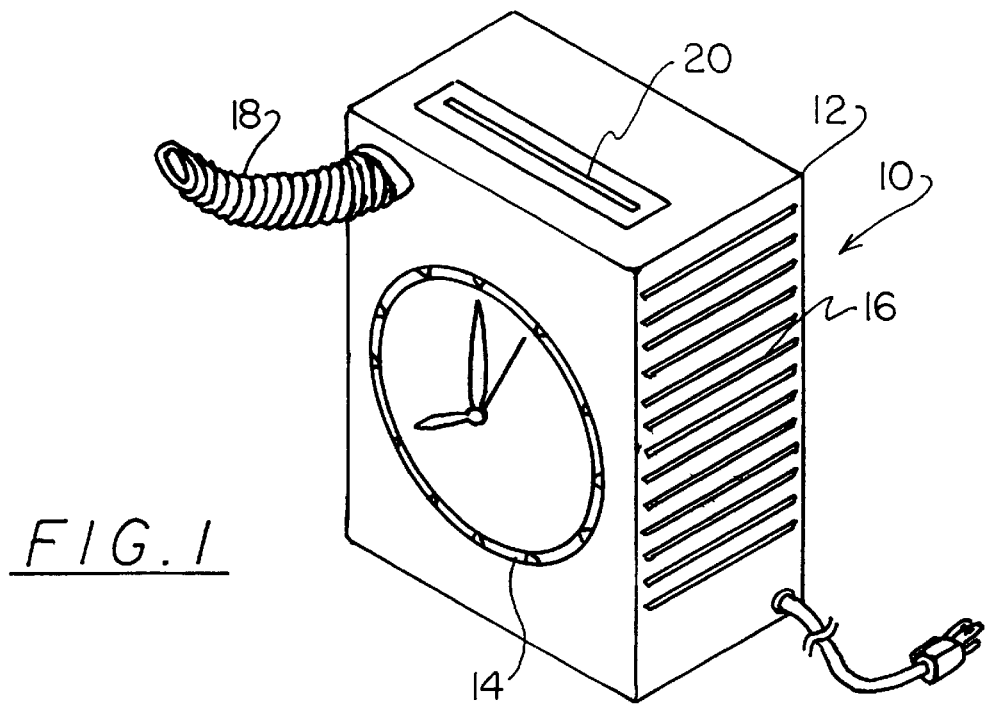
FIG. 1 is a perspective view of a new time clock breathalyzer combination according to the present invention.
Figure 2:
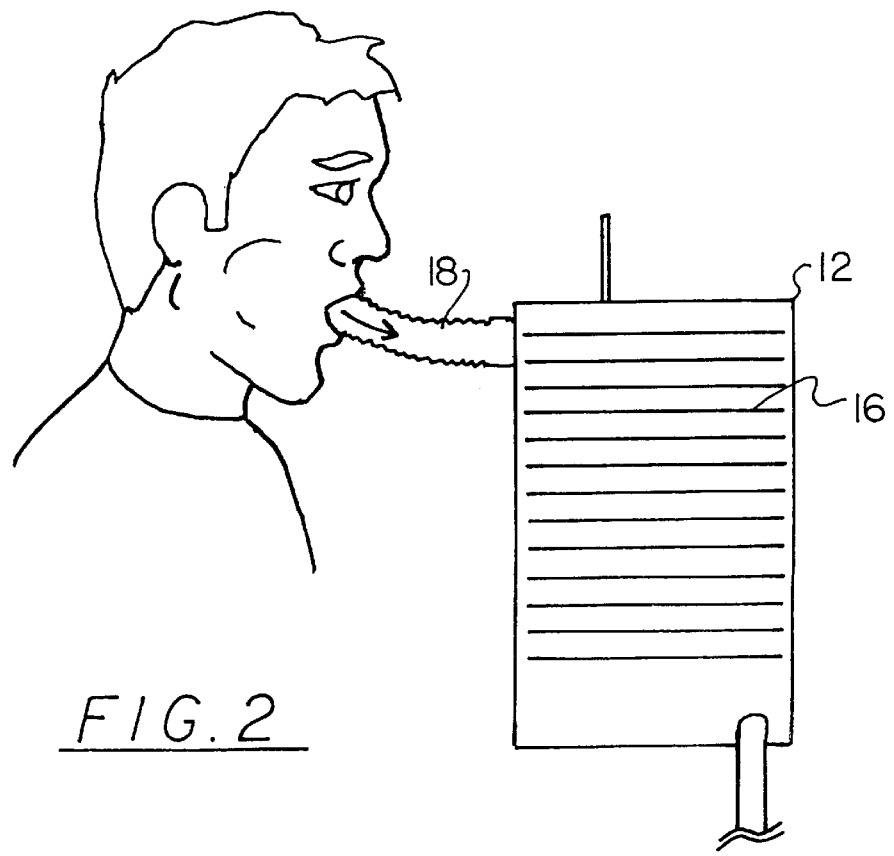
FIG. 2 is a side view of the present invention.

With reference now to the drawings, and in particular to FIGS. 1 through 4 thereof, a new time clock breathalyzer combination embodying the principles and concepts of the present invention and generally designated by the reference numeral 10 will be described.

The present invention, designated as numeral 10, includes a housing 12 with a rectangular configuration having a front face, a rear face, a top face, a bottom face, and a pair of side faces. As shown in FIG. 1, the front face of the housing has a clock 14 mounted thereon for tracking a current time and visually indicating the same. Further, a first one of the side faces has a plurality of vertically spaced horizontally oriented slots 16 formed therein for storing a plurality of timecards 17 therein. The front face has a flexible bellowed inlet tube 18 with an inboard end coupled to the front face adjacent to the top face and a second one of the side faces. In the preferred embodiment, a plurality of inlet tubes are provided each removably mounted to an inlet port formed on the housing. Each of such inlet tubes would be used by separate employees. The top face further has a slot 20 formed therein for releasably receiving one of the timecards.

Situated within the housing is an air flow rate sensor 22 that is connected to the inboard end of the inlet tube for determining a rate of air flow therethrough. Associated therewith is an alcohol sensor 24 situated within the housing and connected to the inboard end of the inlet tube. In use, the alcohol sensor is adapted for determining an amount of alcohol in the air flow. Also positioned within the housing is a printer 26 for printing characters on the timecard when inserted therein.

Figures 3, 4:
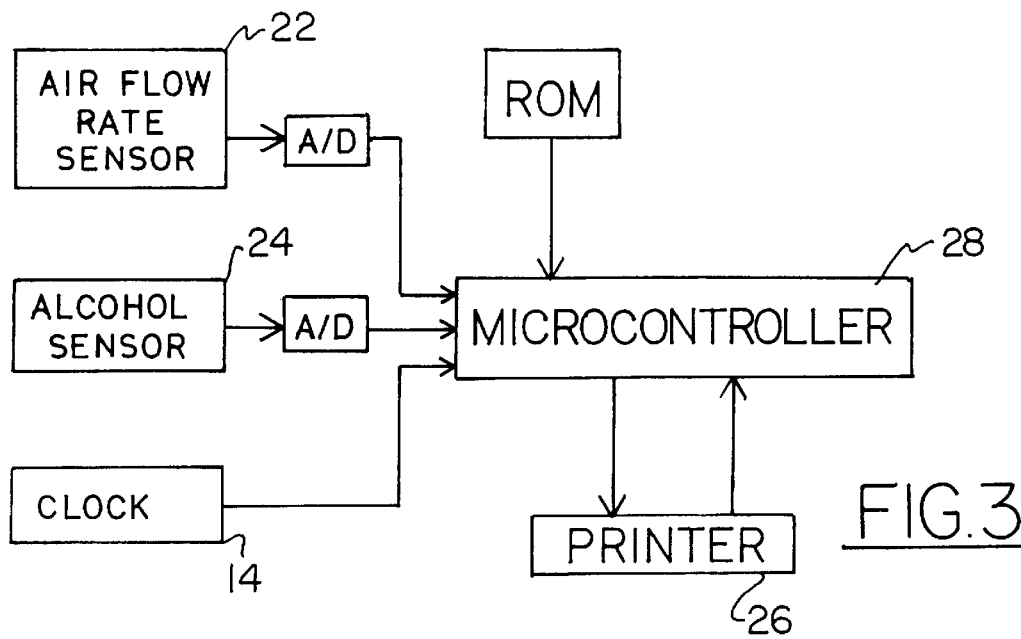
FIG. 3 is a schematic diagram of the present invention.
FIG. 4 is a front view of one of the time cards of the present invention after the printer has printed thereon.

As shown in FIG. 3, a controller 28 is situated within the housing and connected to the air flow rate sensor, alcohol sensor, and printer. Ideally, analog-to-digital converters are connected between the air flow rate sensor, alcohol sensor, and the controller. Further, read only memory is preferably also connected to the controller for providing instructions thereto during use. The read only memory is also adapted for storing conversion data for use by the alcohol sensor.

In use, the controller serves to calculate an alcohol percentage amount within a user from the amount of alcohol detected by the alcohol sensor. Such calculation is only carried out upon the detection of a sufficient air flow rate by the air flow rate sensor, thereby insuring that a sufficient sample is received prior to beginning. The alcohol sensor thus gives an estimation of a blood alcohol level of the user.

The controller is further adapted to print the alcohol percentage amount and a time of beginning work upon a first insertion of one of the timecards within the slot of the housing. Upon a subsequent second insertion of the time card within the slot of the housing, the controller is further adapted to print the alcohol percentage amount and a time of ending work. Note FIG. 4. Regardless of whether the work ending or working beginning time is being recorded, the timecard must be inserted within the slot before the calculation of alcohol percentage amount will take place by the alcohol sensor. A sensor may be positioned within the housing for indicating the insertion of the timecard. Further, the alcohol percentage amount must be calculated prior to the printer printing the work beginning and ending times.

Finally, alert indicia is printed on a top of the timecard upon the alcohol percentage amount being greater than a predetermined amount. Ideally, indicia such as "GO HOME" is printed on the time card for providing a hard copy indication that worker is unfit to work.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A combined time clock breathalyzer comprising, in combination:

a housing with a rectangular configuration having a front face, a rear face, a top face, a bottom face, and a pair of side faces, the front face having a clock mounted thereon for tracking a current time and visually indicating the same, a first one of the side faces having a plurality of vertically spaced horizontally oriented slots formed therein for storing a plurality of timecards therein, the front face having a flexible bellowed inlet tube with an inboard end coupled to the front face adjacent to the top face and a second one of the side faces, the top face having a slot formed therein for releasably receiving one of the timecards;

an air flow rate sensor situated within the housing and connected to the inboard end of the inlet tube for determining a rate of air flow therethrough;

an alcohol sensor situated within the housing and connected to the inboard end of the inlet tube for determining an amount of alcohol in the air flow;

a printer positioned within the housing adjacent to the slot of the housing for printing characters on the timecard when inserted therein; and a controller situated within the housing and connected to the air flow rate sensor, alcohol sensor, and printer, the controller adapted to calculate an alcohol percentage amount within a user from the amount of alcohol detected by the alcohol sensor upon the detection of a sufficient air flow rate by the air flow rate sensor, the controller further adapted to print the alcohol percentage amount and a time of beginning work upon a first insertion of one of the timecards within the slot of the housing and print the alcohol percentage amount and a time of ending work upon a subsequent second insertion of the timecard within the slot of the housing, wherein alert indicia is printed on a top of the timecard upon the alcohol percentage amount being greater than a predetermined amount.

2. A combined time clock breathalyzer comprising, in combination:

a clock for tracking a current time;

an inlet port;

an alcohol sensor connected to the inlet port for determining an amount of alcohol in an air flow;

a printer;

a controller adapted to calculate an alcohol percentage amount within a user from the amount of alcohol detected by the alcohol sensor, the controller further adapted to provide an indication upon the alcohol percentage amount being greater than a predetermined amount; and a housing with a having a front face, a rear face, a top face, a bottom face, and a pair of side faces, the clock being mounted to the front face of the housing, a first one of the side faces having a plurality of vertically spaced horizontally oriented slots formed therein for storing a plurality of timecards therein, the front face having a flexible bellowed inlet tube with an inboard end coupled to the front face adjacent to the top face and a second one of the side faces, the top face having a slot formed therein for releasably receiving one of the timecards.

3. A combined time clock breathalyzer as set forth in claim 2 wherein the indication is in the form of printing indicia on one of said timecards via the printer.

4. A combined time clock breathalyzer as set forth in claim 2 and further including an air flow rate sensor connected to the inlet port for determining a rate of air flow therethrough.

5. A combined time clock breathalyzer as set forth in claim 2 wherein the controller is adapted to print the alcohol percentage amount on one of said timecards.

6. A combined time clock breathalyzer as set forth in claim 2 wherein the controller is adapted to print the alcohol percentage amount on one of said timecards along with a current time.

7. A combined time clock breathalyzer comprising:

a housing having a front face, a rear face, a top face, a bottom face, and a pair of side faces, the front face having a clock mounted thereon for tracking a current time and visually indicating the same, a first one of the side faces having a plurality of slots formed therein for storing a plurality of timecards therein, a flexible bellowed inlet tube with an inboard end coupled to the housing, a slot formed in the housing for releasably receiving one of the timecards;

an air flow rate sensor situated in the housing and connected to the inboard end of the inlet tube for determining a rate of air flow therethrough;

an alcohol sensor situated in the housing and connected to the inboard end of the inlet tube for determining an amount of alcohol in the air flow;

a printer positioned in the housing adjacent to the slot of the housing for printing characters on the timecard when inserted therein; and a controller situated in the housing and connected to the air flow rate sensor, alcohol sensor, and printer, the controller adapted to calculate an alcohol percentage amount within a user from the amount of alcohol detected by the alcohol sensor upon the detection of a sufficient air flow rate by the air flow rate sensor, the controller further adapted to print the alcohol percentage amount and a time of beginning work upon a first insertion of one of the timecards in the slot of the housing and print the alcohol percentage amount and a time of ending work upon a subsequent second insertion of the timecard within the slot of the housing, wherein alert indicia is printed on a top of the timecard upon the alcohol percentage amount being greater than a predetermined amount.

* * * * *